US00PP16531P2

(12) United States Plant Patent
Kister

(10) Patent No.: US PP16,531 P2
(45) Date of Patent: May 9, 2006

(54) ***NEPHROLEPIS* PLANT NAMED 'SUNJEST'**

(50) Latin Name: *Nephrolepis obliterata*
Varietal Denomination: Sunjest

(75) Inventor: John Kister, Fallbrook, CA (US)

(73) Assignee: Sunlet Nursery, Inc., Fallbrook, CA (US)

( * ) Notice: Subject to any disclaimer, the term of this patent is extended or adjusted under 35 U.S.C. 154(b) by 19 days.

(21) Appl. No.: 11/055,809

(22) Filed: Feb. 11, 2005

(51) Int. Cl.
*A01H 5/00* (2006.01)

(52) U.S. Cl. ..... Plt./379

(58) Field of Classification Search ..... Plt./379
See application file for complete search history.

(56) References Cited

U.S. PATENT DOCUMENTS

PP14,995 P2 * 7/2004 Van Andel ..... Plt./379

* cited by examiner

*Primary Examiner*—Kent L. Bell
*Assistant Examiner*—W. C. Haas
(74) *Attorney, Agent, or Firm*—C. A. Whealy

(57) ABSTRACT

A new and distinct cultivar of *Nephrolepis* plant named 'Sunjest', characterized by its mostly upright and somewhat outwardly arching plant habit; uniform and symmetrical in form; compact and dense growth habit; fronds that are somewhat curled with flexible rachis; and dark green-colored pinnae that are incised and spaced closely together.

2 Drawing Sheets

Botanical designation: *Nephrolepis obliterata.*
Cultivar denomination: 'Sunjest'.

BACKGROUND OF THE INVENTION

The present invention relates to a new and distinct cultivar of *Nephrolepis* fern plant, botanically known as *Nephrolepis obliterata,* and hereinafter referred to by the name 'Sunjest'.

The new *Nephrolepis* fern is a naturally-occurring whole plant mutation of the *Nephrolepis obliterata* cultivar Kimberly Queen, not patented. The new *Nephrolepis* fern was discovered by the Inventor in a controlled environment in Fallbrook, Calif. in June, 2003.

Since August, 2003, asexual reproduction by divisions of the new *Nephrolepis* fern in a controlled environment at Fallbrook, Calif. has shown that the unique features of this new *Nephrolepis* fern are stable and retained through successive generations of asexual reproduction.

SUMMARY OF THE INVENTION

The new *Nephrolepis* fern has not been observed under all possible environmental conditions. The phenotype may vary somewhat with variations in environment such as temperature and light intensity without, however, any variance in genotype. The following observations, measurements and comparisons describe plants grown in Fallbrook, Calif., under conditions generally used in commercial practice.

The following traits have been repeatedly observed and are determined to be the unique characteristics of 'Sunjest'. These characteristics in combination distinguish 'Sunjest' as a new and distinct cultivar of *Nephrolepis:*

1. Mostly upright and somewhat outwardly arching plant habit; uniform and symmetrical in form.
2. Compact and dense growth habit.
3. Fronds that are somewhat curled with flexible rachis.

4. Dark green-colored pinnae that are incised and spaced closely together.

The new *Nephrolepis* fern is most similar to its parent cultivar, the cultivar Kimberly Queen. However, in side-by-side comparisons conducted in Fallbrook, Calif., the new *Nephrolepis* fern differed from plants of the cultivar Kimberly Queen in the following characteristics:

1. Plants of the new *Nephrolepis* fern were more compact and denser than plants of the cultivar Kimberly Queen.
2. Plants of the new *Nephrolepis* fern had shorter fronds and pinnae than plants of the cultivar Kimberly Queen.
3. Fronds and pinnae of plants of the new *Nephrolepis* fern were curled whereas fronds and pinnae of plants of the cultivar Kimberly Queen were straight.

The new *Nephrolepis* fern can be compared to plants of the *Nephrolepis* cultivar Nr. 21, disclosed in U.S. Plant Pat. No. 14,995. However, in side-by-side comparisons, the new *Nephrolepis* fern differed from plants of the cultivar Nr. 21 in the following characteristics:

1. Plants of the new *Nephrolepis* fern were more compact than plants of the cultivar Nr. 21.
2. Fronds of plants of the new *Nephrolepis* fern were curled whereas fronds of plants of the cultivar Nr. 21 were straight.
3. Pinnae of plants of the new *Nephrolepis* fern and the cultivar Nr. 21 differed in pinnae coloration.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Nephrolepis* fern.

The photograph on the first sheet comprises a side perspective view of a typical plant of 'Sunjest'.

The photograph on the second sheet is a close-up view of typical fronds of 'Kimberly Queen' (left) and 'Sunjest' (right).

DETAILED BOTANICAL DESCRIPTION

Plants in the aforementioned photographs and used in the following description were grown under conditions which closely approximate commercial production conditions during the late summer and early fall in 15-cm containers in a polypropylene-covered shadehouse in Fallbrook, Calif. During the production of the plants, day temperatures ranged from 21e ° C to 29.5° C., night temperatures ranged from 15.5° C. to 19° C. and light levels were about 2,800 footcandles. Plants in the photographs and used for the description were about 18 weeks old when the photographs and description were taken. In the description color references are made to The Royal Horticultural Society Colour Chart, 1986 Edition, except where general terms of ordinary dictionary significance are used.

Botanical classification: *Nephrolepis obliterata* cultivar Sunjest.

Parentage: Naturally-occurring whole plant mutation of *Nephrolepis obliterata* cultivar Kimberly Queen, not patented.

Propagation: By tissue culture.

*Time to initiate roots.*—About three weeks at 18.3° C.

*Time to produce a rooted young plant, summer.*—About nine weeks at 26.6° C.

*Time to produce a rooted young plant, winter.*—About eleven weeks at 26.6° C.

*Root description.*—Fine, fibrous; dark brown in color.

*Rooting habit.*—Freely branching; dense.

Plant description:

*Growth habit.*—Mostly upright and somewhat outwardly arching plant habit; uniform and symmetrical in form. Compact and dense growth habit. Vigorous.

*Plant height.*—About 32 cm from soil line to top of plant plane.

*Plant width.*—About 44 cm.

*Frond description.*—Leaf arrangement: Bi-pinnate. Frond length: About 32 cm. Frond width: About 6 cm. Rachis length: About 32 cm. Rachis diameter: About 1.5 mm. Rachis strength: Strong; flexible. Rachis texture: Pubescent. Rachis/frond orientation: Curling; apex, recurved. Rachis color: 137B to 137C.

*Pinnae description.*—Shape: Roughly deltoid, elongate, narrow. Length: About 3 cm. Width: About 6 to 8 mm. Quantity of pinnae: About 100 per frond. Apex: Acuminate. Base: Truncate. Margin: Towards the apex, irregularly incised; towards the base, entire. Aspect: Curling; undulate. Attachment: Sessile. Texture, upper and lower surfaces: Smooth, glabrous. Venation pattern: Pinnate. Color: When developing, upper surface: 141B. When developing, lower surface: 146B. Fully developed, upper surface: 137A; venation, 137A. Fully developed, lower surface: 137B; venation, 137A.

*Spores.*—None observed.

Disease/pest resistance: Resistance to pathogens and pests common to *Nephrolepis* ferns has not been observed.

Temperature tolerance: Plants of the new *Nephrolepis* fern have been observed to be tolerant to temperatures ranging from about −1° C. to about 43° C.

It is claimed:

1. A new and distinct cultivar of *Nephrolepis* plant named 'Sunjest', as illustrated and described.

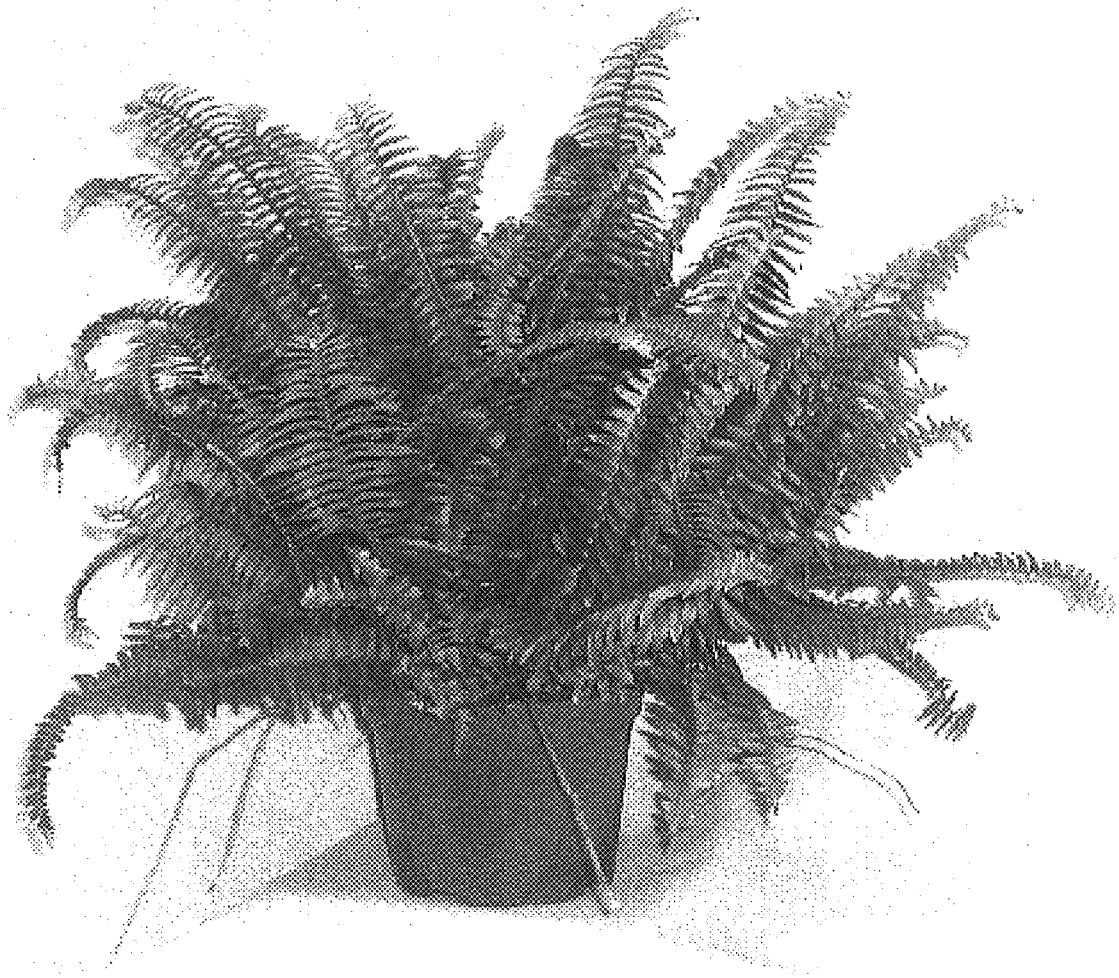

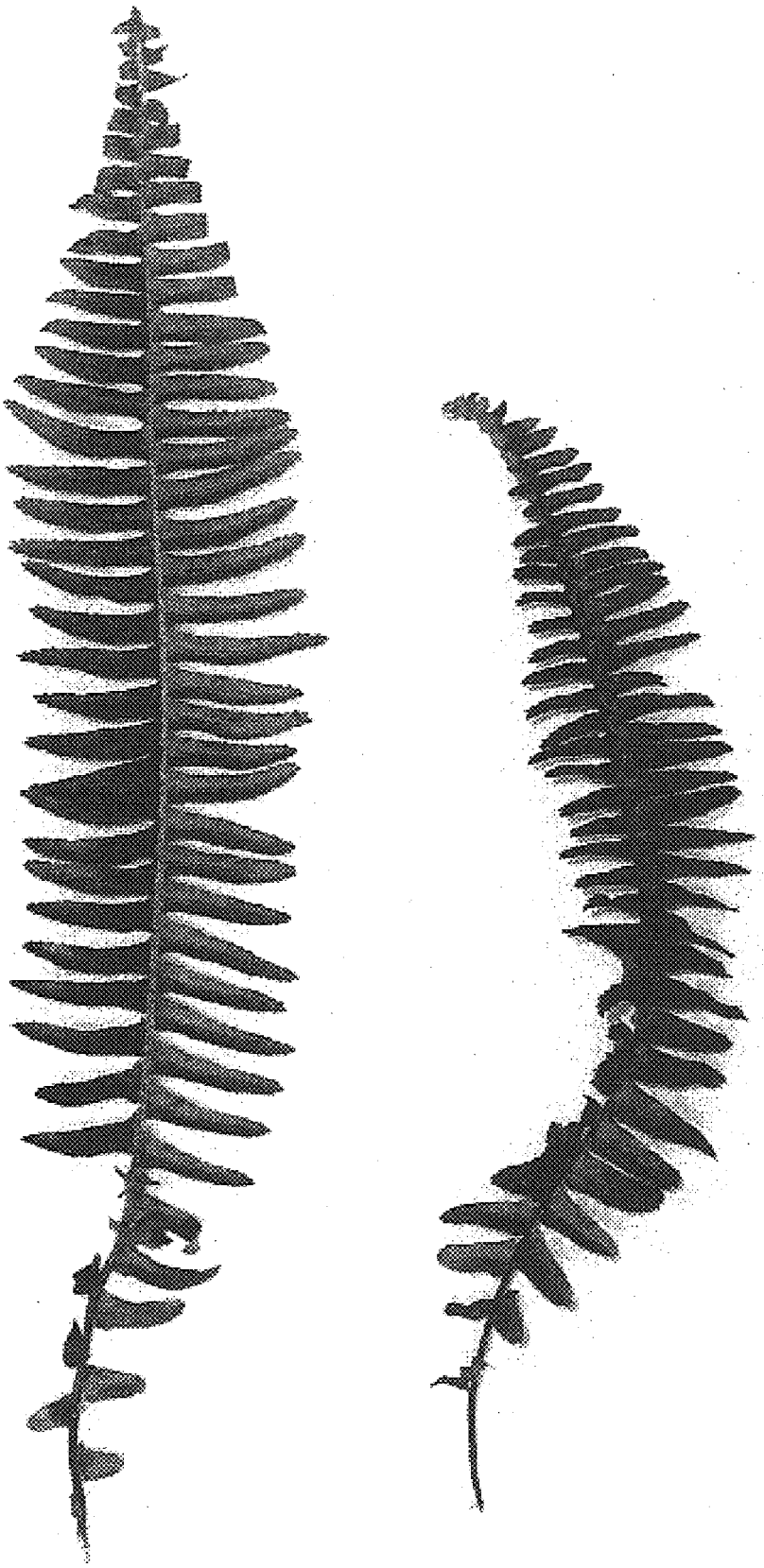

* * * * *